US006964663B2

(12) United States Patent
Grant et al.

(10) Patent No.: US 6,964,663 B2
(45) Date of Patent: Nov. 15, 2005

(54) COMBINATION BONE FIXATION/IMMOBILIZATION APPARATUS

(75) Inventors: William Peter Grant, Virginia Beach, VA (US); Laurence Glenn Rubin, Richmond, VA (US); Steve Cook, Richmond, VA (US); Guy Richard Pupp, Bloomfield Hills, MI (US)

(73) Assignee: EZ Concepts Surgical Device Corporation, Richmond, VA (US)

( * ) Notice: Subject to any disclaimer, the term of this patent is extended or adjusted under 35 U.S.C. 154(b) by 140 days.

(21) Appl. No.: 10/663,263

(22) Filed: Sep. 16, 2003

(65) Prior Publication Data

US 2005/0059968 A1   Mar. 17, 2005

(51) Int. Cl.⁷ ............................................. A61B 17/56
(52) U.S. Cl. ............................. 606/54; 606/57; 606/59
(58) Field of Search ............................. 606/54, 53, 55, 606/56, 57, 58, 59; 602/26, 27, 28, 29

(56) References Cited

U.S. PATENT DOCUMENTS

| | | | |
|---|---|---|---|
| 6,214 A | 3/1849 | Yerger | |
| 67,493 A | 8/1867 | Burch | |
| 604,044 A | 5/1898 | Hamel et al. | |
| 1,863,788 A | 6/1932 | Clash | |
| 2,020,262 A | 11/1935 | Longfellow | |
| 2,035,952 A | 3/1936 | Ettinger | |
| 2,079,567 A * | 5/1937 | Anderson | 602/39 |
| 2,393,831 A | 1/1946 | Stader | |
| 3,557,782 A | 1/1971 | Wafer | |
| 4,166,460 A | 9/1979 | Applegate | |
| 4,338,927 A * | 7/1982 | Volkov et al. | 606/56 |
| 4,351,324 A | 9/1982 | Bronkhorst | |
| 4,378,793 A | 4/1983 | Mauldin et al. | |
| 4,446,856 A | 5/1984 | Jordan | |
| 4,604,996 A | 8/1986 | Nunamaker et al. | |
| 4,923,458 A | 5/1990 | Fisher | |
| 5,070,868 A * | 12/1991 | Hepburn et al. | 602/27 |
| 5,087,258 A | 2/1992 | Schewior | |
| 5,092,321 A * | 3/1992 | Spademan | 602/27 |
| 5,176,623 A * | 1/1993 | Stetman et al. | 602/27 |
| 5,261,873 A | 11/1993 | Bremer et al. | |
| 5,368,551 A | 11/1994 | Zuckerman | |
| 5,370,133 A | 12/1994 | Darby et al. | |
| 5,399,152 A | 3/1995 | Habermeyer et al. | |
| 5,496,319 A | 3/1996 | Allard et al. | |
| 5,520,627 A * | 5/1996 | Malewicz | 602/26 |
| 5,578,041 A | 11/1996 | Nash et al. | |
| 5,609,570 A | 3/1997 | Lamont | |
| 5,827,210 A | 10/1998 | Antar et al. | |
| 5,833,639 A * | 11/1998 | Nunes et al. | 602/23 |
| 6,328,737 B1 | 12/2001 | Moorcroft et al. | |

* cited by examiner

*Primary Examiner*—Pedro Philogene
(74) *Attorney, Agent, or Firm*—John H. Thomas, P.C.

(57) ABSTRACT

A combination bone fixation/immobilization apparatus is adapted to stabilize a patient's foot and ankle. A foot plate is adapted to have one or more transfixation wires or pins or screws fixed thereto. A substantially rigid leg support assembly is adapted to receive a patient's leg, the leg support comprising a cuff and a strap adapted to secure the cuff around the patient's leg. The leg support is rigidly attached to the foot plate. A patient's foot may thereby be fixed with transfixation wires, or pins or screws and simultaneously immobilized with respect to the ankle and lower leg.

16 Claims, 10 Drawing Sheets

COMBINATION BONE FIXATION/IMMOBILIZATION APPARATUS

The present invention relates to therapeutic orthopedic devices for fixating and immobilizing limbs, and specifically a patient's foot and ankle. The invention includes features of both bone fixator apparatuses and external, immobilizing braces and/or orthotics.

BACKGROUND OF THE INVENTION

There are many types and classes of braces and other orthopedic devices for fixating and immobilizing patient's limbs. Specifically in the field of foot and ankle surgery and recovery, there are multiple types of options for a care giver to stabilize a patient's foot after surgery. These braces include complicated bone fixators that have transfixation wires or pins or screws that extend into and through bone segments in order to stabilize them. Other external braces including a wide range of removable casts and ankle braces are also known.

One class of procedures was originally developed by a surgeon Dr. Ilizarov that includes the use of thin wire external fixators to move segments of bone for purposes of reconstruction of fractured or deformed extremities during orthopedic surgery. Frames used in these types of procedures are arranged crosswise in pairs or individually in each ring or ring-section level, whereby the various rings are connected to each other by means of rods and bolts, and the intervals of the ring levels are adjusted by rods of different lengths, by rods whose lengths can be varied telescopically, or by bolts that can be adjusted. A basic principle of the hybrid frames used in these types of procedures is that they may move portions of the anatomic skeleton of a patient by virtue of distraction or compression. These hybrid-type frames are now frequently in use for orthopedic applications including, but not limited to, limb lengthening, stabilization and positioning of open fractures, and in the structural correction of a multitude of lower extremity deformities including, but not limited to, correction of angulation, rotation and translation. In each case, there is use of a footplate that places wires across different segments of a patient's foot (hindfoot, midfoot, and forefoot) that are then used to distract or compress the segments of the foot for structural realignment. (There are in fact many types of procedures that may use these types of apparatuses.) In each of these systems, this footplate is connected to a ring (one or more rings) around the lower leg of the patient for stability and spatial relation with respect to the foot. If the patient's foot plate was used by itself, the patient's foot could articulate at the ankle joint, and there would be no stability at the ankle joint. Much of the intended correction could inherently then be lost and the patient would have an unsatisfactory way to hold the foot in a therapeutically correct position. Accordingly, one or two rings or partial rings are placed around the lower leg or ankle, and the foot plate is connected to the leg to hold all the structures in an anatomically rigid position ideal for healing. Additionally, rigidly stabilizing the foot plate with respect to the ankle permits early ambulation in major foot reconstructive surgery.

Medical risks associated with these Ilizarov-type procedures and associated apparatuses include the requirement of pins or wires or screws connected to the tibia and fibula, thereby presenting the possibility of infection, fracture and nerve or vessel damage in the lower leg. Use of these frames are also inherently far more complicated with respect to care and recovery. Finally, use of these hybrid frames requires a lengthy and difficult surgery that requires specialized training.

Another general type of orthopedic device that may be used as a therapeutic or surgical recovery brace is commonly know as a cam boot. This type of boot is a functional splint or cast which holds the foot in a neutral position while healing takes place after a surgery. A cam boot is noninvasive and successfully can immobilize the extremity during the healing process. Also, cam boots are removable and have a distinct hygiene advantage over predecessor casts. While appropriate in many situations and for multiple types of surgeries, a cam boot is not an option when performing surgeries to correct many foot deformities.

SUMMARY OF THE INVENTION

Accordingly, it is an object of the present invention to provide an apparatus for stabilizing a patient's foot and ankle in a manner that overcomes the foregoing drawbacks. The present invention is directed to the combination of a foot plate together with a rigid leg support.

In one embodiment, the invention includes a combination bone fixation/immobilization apparatus adapted to stabilize a patient's foot and ankle. The apparatus includes a foot plate adapted to have a plurality of transfixation wires fixed thereto. The apparatus further includes a substantially rigid leg support assembly adapted to receive a patient's leg, the leg support comprising a cuff and a strap adapted to secure the cuff around the patient's leg. The leg support is rigidly attached to the foot plate, whereby a patient's foot may be fixed with transfixation wires, and the foot is simultaneously immobilized with respect to the ankle and lower leg. The apparatus may further comprise a foot support assembly rigidly attached to the foot plate and adapted to support the sole of a patient's foot. The leg support may include a liner foreplate. The apparatus may include a variable, adjustable height connection between the foot plate and the foot support. The apparatus may include a three-point attachment of the leg support to the foot plate. The leg support may comprise an air filled or a fluid filled bladder. The leg support may be attached to the foot plate in a generally perpendicular position to a plane including the foot plate.

In an alternative embodiment of the present invention, a combination bone fixation/mobilization apparatus is adapted to stabilize a patient's foot and ankle. The apparatus includes a foot plate adapted to have a plurality of transfixation wires fixed thereto. The apparatus further comprises a substantially rigid leg support assembly adapted to receive a patient's leg, the support comprising a cuff and a strap adapted to secure to the cuff around the patient's leg. The assembly still further comprises a foot support assembly rigidly attached to the leg support and adapted to support the sole of a patient's foot. The foot plate is adapted to be positioned at least partially around and outside the leg and foot support assemblies. The leg support may further include a liner foreplate. The leg support may further comprise an air, other gases, gel, foam or fluid filled bladder. The leg support may be attached to the foot support in a generally perpendicular position to a plane including the foot support. The leg support and foot support may be a single, continuous piece. The apparatus may further comprise a positioning rod connected on one end to the leg support and on the opposite end to the foot support. The rigid attachment between the leg support and the foot support may be a hinge.

DETAILED DESCRIPTION OF EMBODIMENTS

The present invention is an apparatus that includes, in part, a combination of technologies of hybrid or circular frames of the type that may be used, for instance, in an Ilizarov procedure and cam walker boots. The apparatus includes a foot plate adapted to have transfixation wires or pins or screws fixed to it. The wires or pins or screws will extend into and/or through the bone segments in a patient's foot. The apparatus further includes a leg support assembly like that found in a cam boot. The leg support embraces the lower leg of a patient. In one embodiment, the leg support is rigidly connected to the foot plate. The resulting apparatus is one that sets the patient's foot in relation to the ankle and lower leg of the patient.

In another embodiment, a leg support and foot support are rigidly attached to each other to secure a patient's foot in relation to their ankle and lower leg. This leg support and foot support apparatus is then used in combination with a foot plate, although the foot plate itself is not connected to either the leg support or foot support apparatus.

Different embodiments of combination bone fixation/ immobilization apparatuses are shown in the various drawings. The differences in structure are merely exemplary of some of the many possible alternative constructions in accordance with the present invention.

Figure 1:
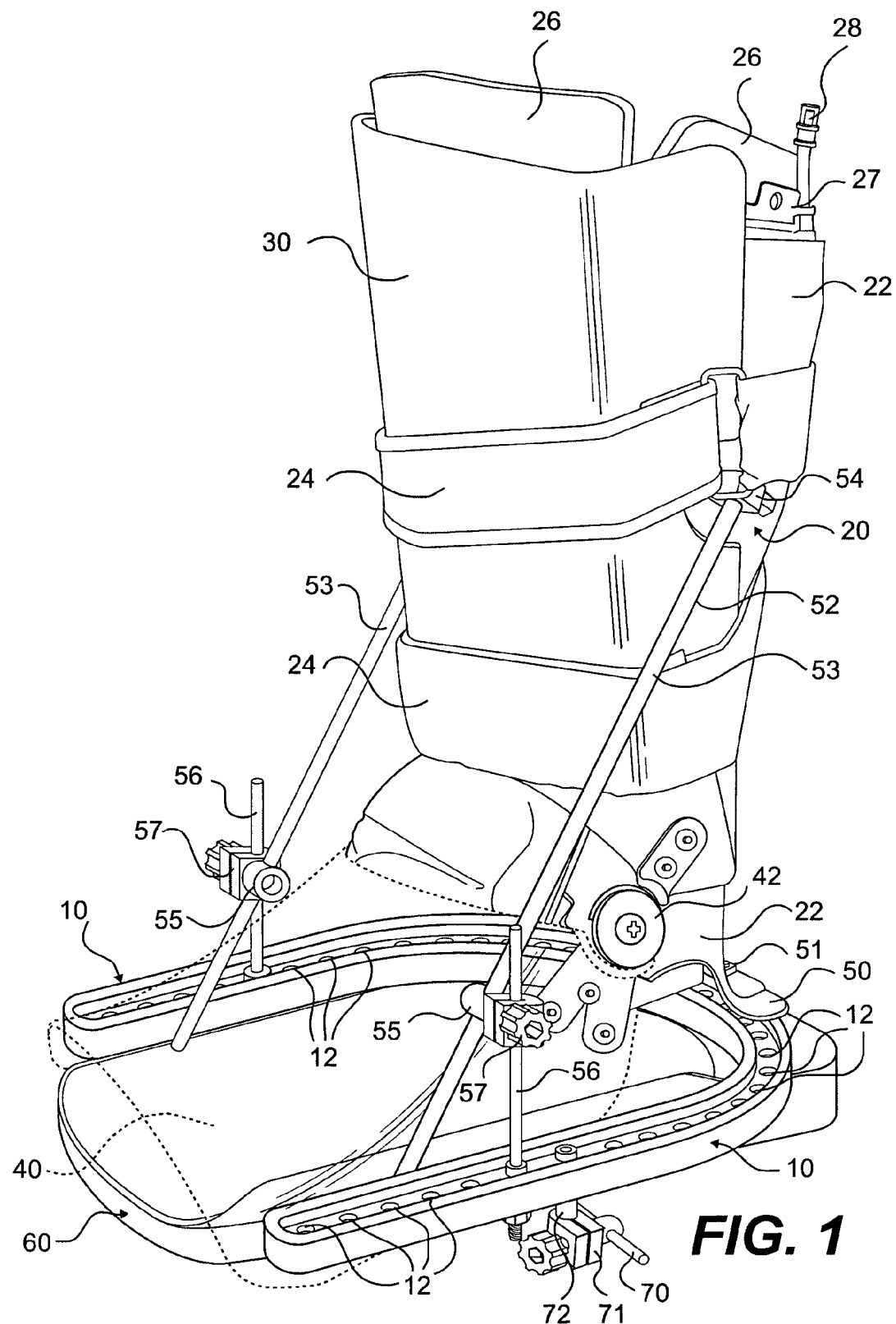
FIG. 1 is perspective view of a first embodiment of an apparatus in accordance with the present invention.
Figure 1A:
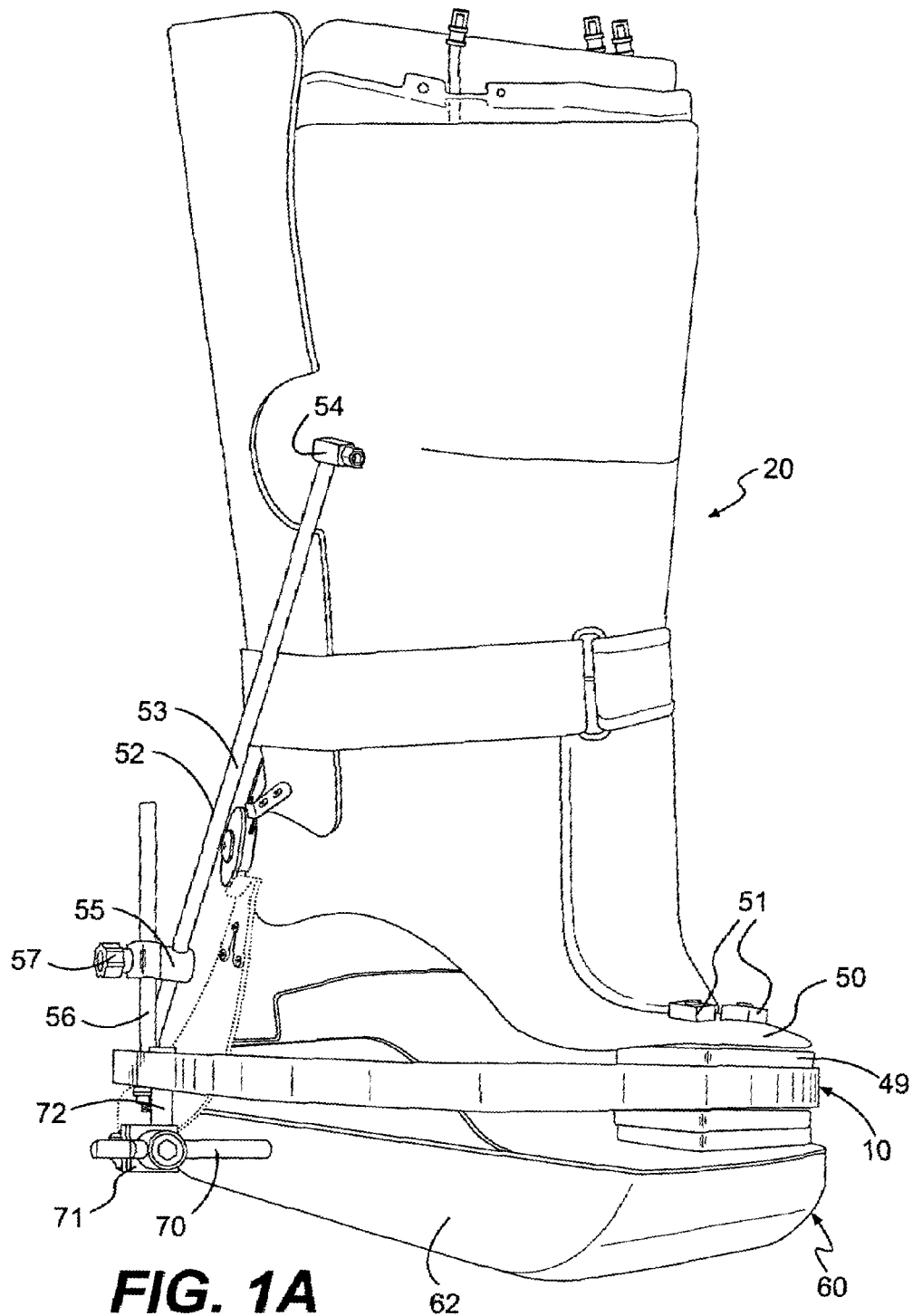
FIG. 1A is a side elevation view from the rear of the apparatus displayed in FIG. 1.
Figure 2:
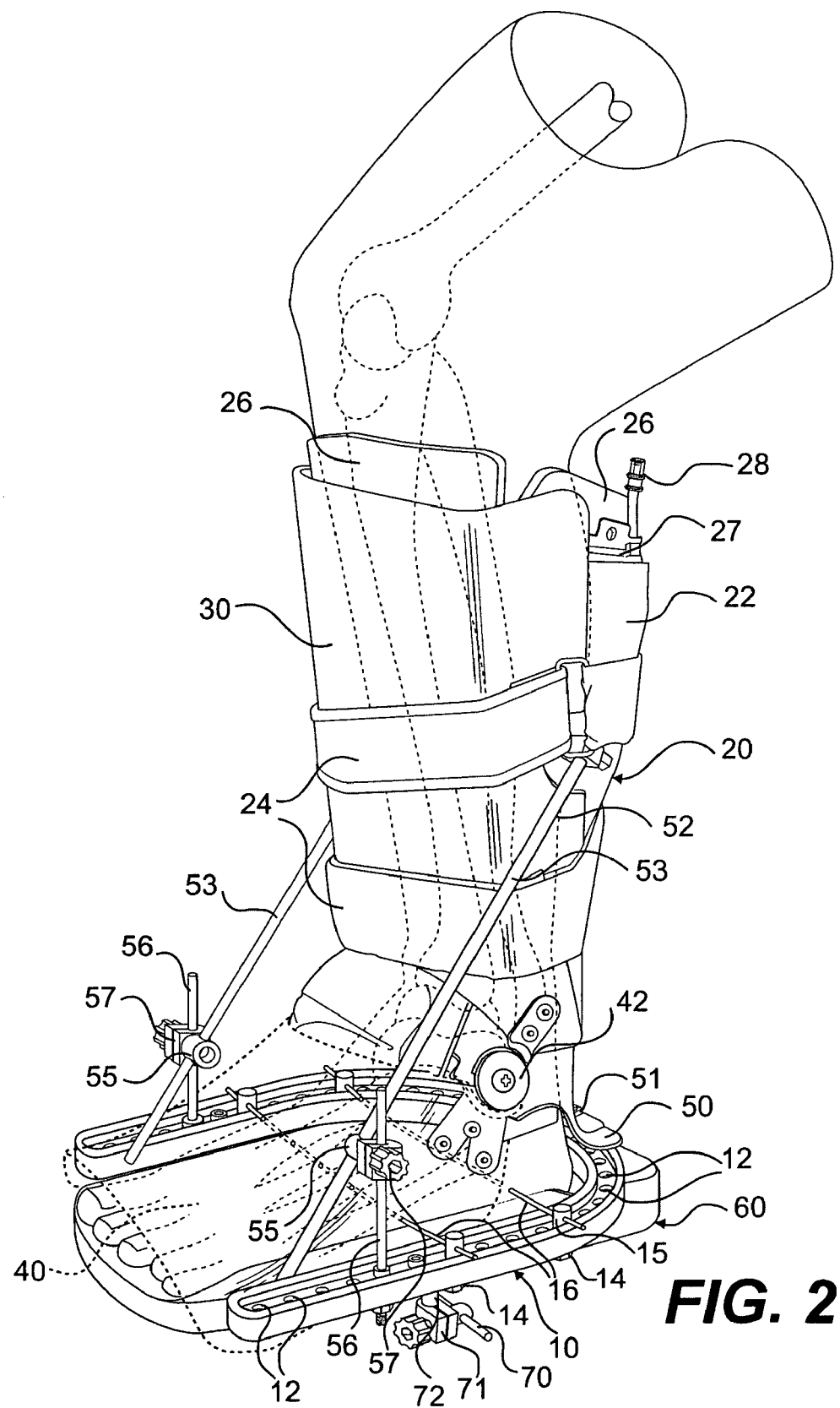
FIG. 2 is a perspective view of the first embodiment of the present invention with a lower leg and foot shown in broken lines in the brace.

Referring first to FIGS. 1, 1A and 2, there is shown a foot plate 10 having a U-shape. The foot plate 10 is a conventional component used in connection with many types of foot surgeries including but not limited to Ilizarov-type procedures. The foot plate 10 is adapted to curve around a patient's heel on the closed end of the foot plate and includes two arms on the open end that are adapted to extend along each side of a patient's foot. A foot plate may have a U-shape, it may be oval, it may be round, it may be symmetrical, it may be asymmetrical, it may be any necessary shape or form necessary for a given surgery. The U-shape foot plate 10 is merely believed to be the most common type of foot plate in use currently.

The foot plate 10 includes apertures 12 that extend vertically through and are located all the way around the U-shape of the foot plate. The apertures 12 are adapted to receive various nuts 14 and bolts 15 and clamps and other mechanical fixtures that secure the transfixation wires 16 that may be used in connection with a foot surgery. (The term "transfixation wires" is used broadly herein to mean wires, pins, screws and any other orthotic device that is adapted to be connected to a foot plate). For purposes of the present invention, the term "foot plate" is defined in its most broad sense to include conventional constructions such as those shown in the drawings but also rail-type devices and other orthotic apparatuses used in foot-related procedures.

Various types of hardware may be used to position the foot plate 10 with respect to a leg support such as leg support 20 and a foot support such as foot support 60. As shown in FIGS. 1 and 2, the foot plate 10 is substantially in a horizontal plane, (i.e. parallel to a floor on which a person might stand). Alternatively, however, the foot plate 10 may be angled or pitched in any direction from the horizontal plane depending on the needs of a patient. The foot plate 10 may be angled so that the rear of the foot plate is higher than the front, or the front of the foot plate may be higher than the rear. Alternatively, the foot plate 10 may be pitched so that the right or left side of the foot plate may be higher than the respective opposite side. Still further, the foot plate 10 may be both angled and pitched. Each of these positions may be medically important in order to obtain the appropriate and successful results for a particular foot procedure.

The leg support 20 is effectively a removable cast or posterior splint for the lower leg of a patient. The leg support 20 is adapted to receive the lower leg of a patient. Lengthwise, it may be any rigid leg support that extends from about the foot all the way up to as high as a patient's thigh. Typically, the leg support 20 includes a reinforcing metal strap or other splint piece to make the leg support rigid enough to support a patient. The leg support 20 includes a cuff 22 that receives and encircles the leg of a patient. The cuff 22 may receive and encircle all or a portion of the leg. In the embodiment shown, the cuff 22 encircles approximately ¾ of the leg. Straps 24 are anchored to the cuff 22 and, using hook and loop construction, may be removably secured around the leg of a patient. An alternative latching structure or any other type of securement strap may be used.

A liner foreplate 30 is fitted around the front of a patient's leg so as to provide a rigid support around the entire leg of a patient. The straps 24 secure the foreplate 30 to the cuff 22. The cuff 22 and foreplate 30 may further include foam padding 26 or other types of cushioning material including a foam molded cushion. The cuff 22 and foreplate 30 may also incorporate a bladder 27 that may be filled with air, other gas, gel, foam or liquid to completely attach or encircle the lower leg for support. As shown in the figures, a bladder valve 28 allows a doctor or user to fill a bladder 27 with air other gas, gel, foam or fluid in order to obtain an appropriate tightness of fit. The padded foam 26 and bladders shown are merely exemplary of many types of padding or combinations of padding that may be used.

The liner foreplate 30 is a preferred construction to be used in conjunction with a cuff 22. The foreplate 30 is easily removed from a patient's leg and allows access to the leg by a doctor or caregiver to a patient. The foreplate 30 may be removed without moving the leg support 20 or foot plate 10.

A footshield 40 is a hard shell that protects the top surface of the foot of a patient from inadvertent or accidental touching or trauma. The footshield 40 is pivotally connected to the liner foreplate 30 by way of hinges 42, or, alternatively, may be of one continuous piece with the foreplate. The footshield 40 is conveniently rotatably connected so that it may be lifted and that a doctor or caregiver may have access to the foot of a patient. Similarly, the footshield 40 is easily removable with the foreplate 30.

In the alternatives shown in FIGS. 1–6, the foot plate 10 must be rigidly connected to the leg support 20 in order to secure the foot and lower leg of a patient in a relative, anatomically correct position. It is this connection of the leg support 20 to the foot plate 10 that determines the position of a patient's foot with respect to their ankle and leg. As every patient is different, and as every surgery is different, the precise attachment of the leg support 20 to the foot plate 10 will vary at the discretion of a doctor. In general terms, foot plate 10 (and the plane including the foot plate) is generally perpendicular to the leg support 20. This is conventional in that a human foot is generally in a plane perpendicular to a leg.

FIGS. 1A, 2, 3, and 3A for instance, demonstrate alternative methods of attaching a leg support 20 to a foot plate 10. FIG. 2 has a 3-point attachment construction. Screws 51 at the heel at the foot plate 10 are attached to an extension portion 50 of the leg support 20. Side connection assemblies 52 connect the leg support 20 to the foot plate 10. The side connection assemblies 52 include angled rods 53 that are connected on one end to the leg support 20 by way of clamps 54, and the other end to the foot plate 10 by way of lower clamps 55. A vertical rod 56 and a vertical rod clamp 57 are further used to join the angled rod 53 in connecting the leg support 20 to the foot plate 10. The use of the vertical rod 56 and vertical rod clamp 57 means that the connection between the leg support 20 and the foot plate 10 may be varied and angled to predetermined degrees from a side view, and may also be pitched to predetermined degrees from a front view. In other words, the height of the vertical rod clamp 57 with respect to the foot plate 10 may be different between the right and left sides of the foot plate. The side connection assembly 52 allows for the leg support 20 be angled forward and backward with respect to the plane including the foot plate 10. The side connection assemblies 52 allow a doctor or surgeon to precisely set both the angle and pitch relationship between a leg support 20 and foot plate 10. Of course, it is also possible to move the foot plate 10 to have different pitches by raising or lowering one of the arms of the "U-shape" versus the other in cases where the foot plate needs to be pitched for medical reasons. Still further alternatively, the heel attachment of the extension 50 to the foot plate 10 may be raised by using shims 49 between the extension and foot plate, or any functionally comparable hardware, to vertically adjust the height of attachment of the extension to the foot plate. The particular types of attachment between the leg support 20 and foot plate 10 are merely exemplary of other types of attachment systems that may be used.

Figure 3:
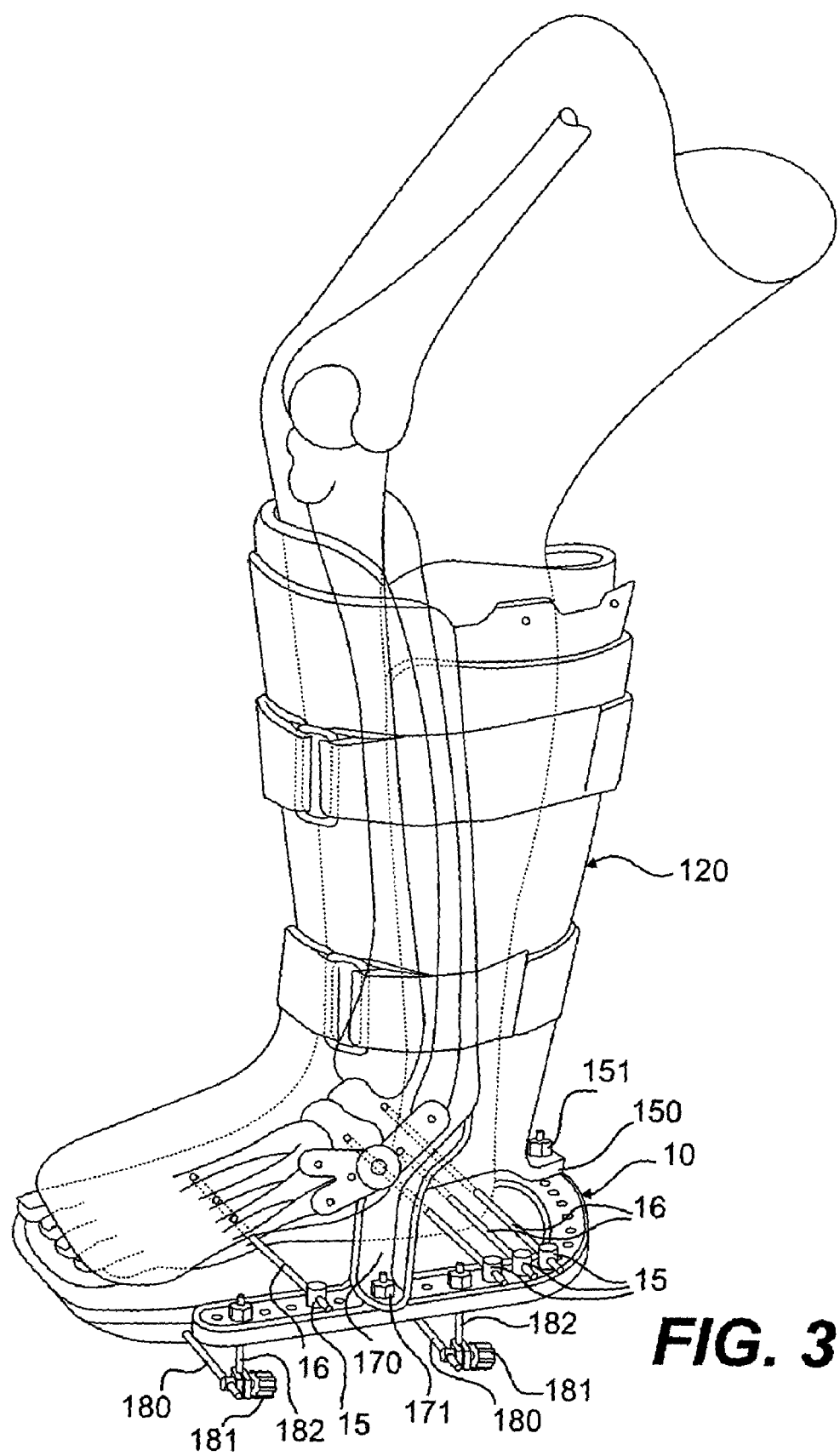
FIG. 3 is a perspective view of a second alternative embodiment of an apparatus in accordance with the present invention.
Figure 3A:
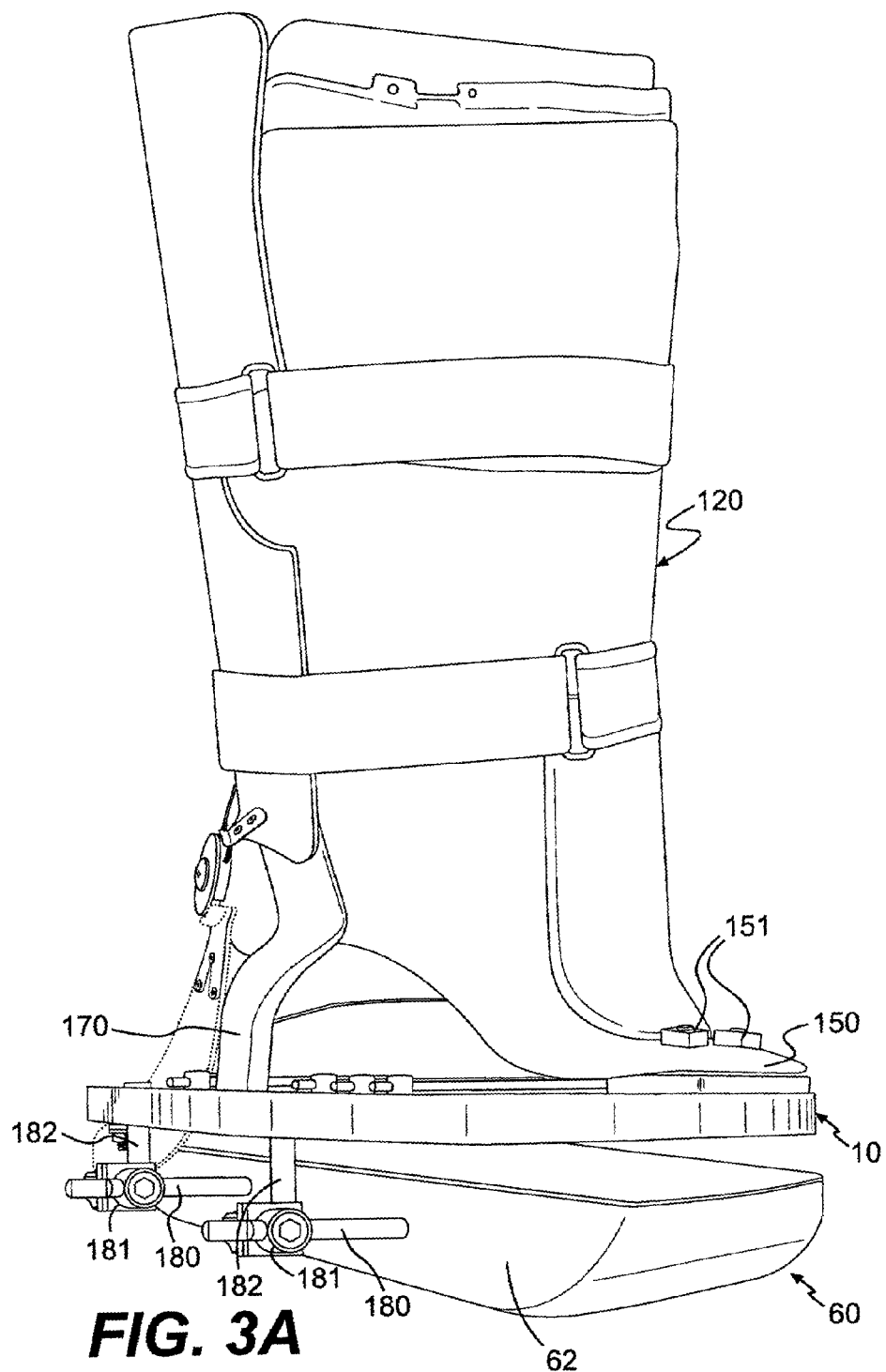
FIG. 3A is a side elevation view from the rear of the apparatus displayed in FIG. 3.

FIGS. 3 and 3A display an alternative structure of a combination bone fixation/immobilization apparatus. There is shown a different type of three-point attachment between a leg support 120 and foot plate 10. (The foot plate 10 is the same in all figures.) In FIG. 3, there are bolts and nuts 151 attached to an extension 150 at the heel connection between the leg support 120 and the foot plate 10. However, there are in this alternative embodiment side extensions 170 that secure the leg support 120 to each side of the foot plate 10 with bolt and nut 171. In this alternative, the variability with respect to angle of mounting and pitch of mounting between the leg support 120 and foot plate 10 can be limited. As noted earlier, however, the angle and pitch may be manipulated by varying other relative features in the components including the foot plate 10.

Figure 4:
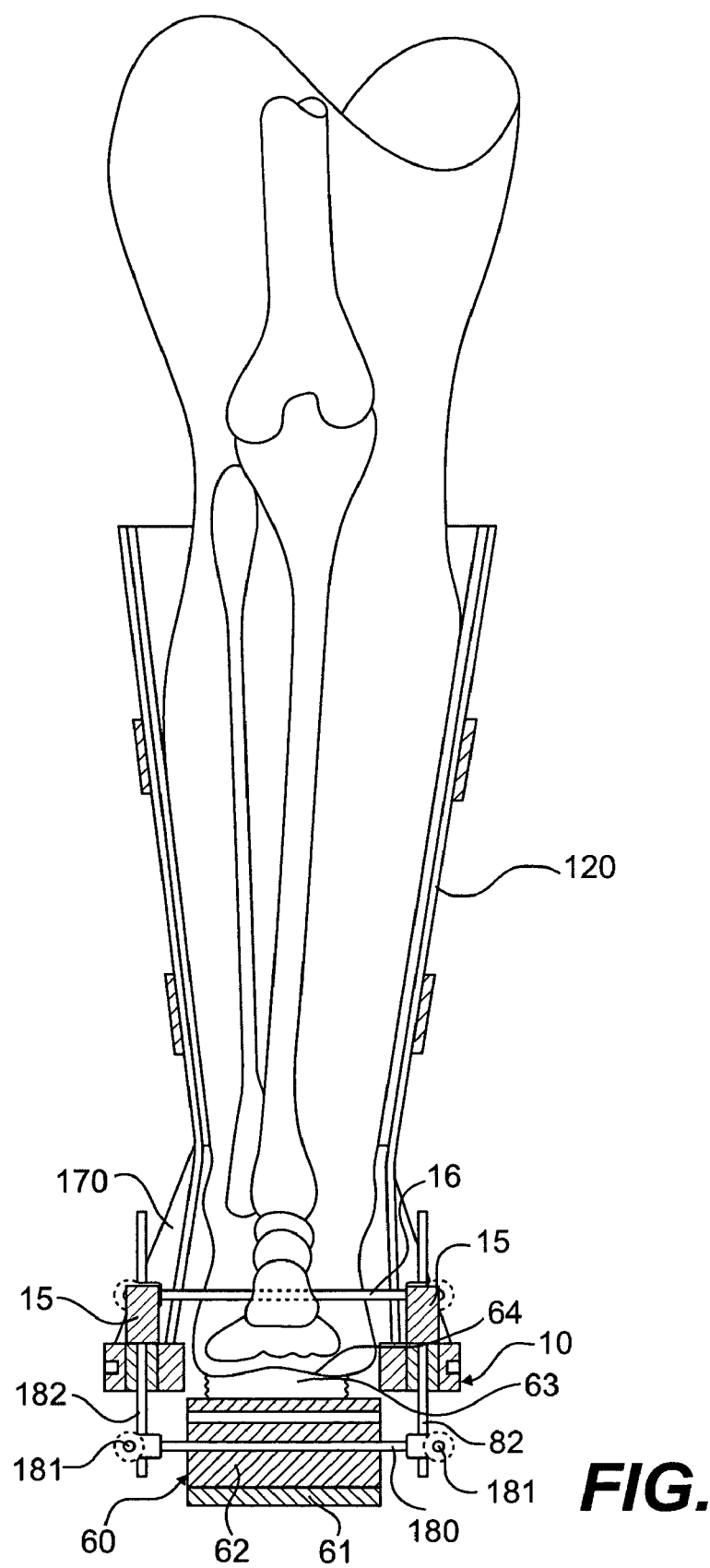
FIG. 4 is a rear elevation, cross sectional view of an apparatus in accordance with the second embodiment of the present invention.

A foot support 60 is conventionally part of the overall apparatus, because it enables and facilitates mobility of a patient. As best shown in FIG. 4, the foot support 60 includes a tread 61 and a hard foam core 62. The tread 61 is merely any conventional rubber or durable sole that allows a person to have traction when they walk. The core 62 is the hard body of the foot support 60. A wedge 63 may be placed on top of core 62 and underneath and adjacent the sole 64 of the foot of a patient. This foam wedge 63 is preferably a removable component. As a foot heals after surgery, more and more weight is allowed to be put on the foot by the patient. This is very simply accomplished by inserting thicker and thicker wedges like wedge 63 that apply pressure to the sole 64 of the foot of a patient.

One cross rod 70 is shown in FIGS. 1, 1A and 2 that is connected by way of clamps 71 and vertical struts 72 to the foot plate 10. This rod 70, in combination with the bolts and screws 51 at the back of the foot support 60, connect the foot plate 10 to the foot support. A pair of cross rods 180 is shown in FIGS. 3 and 3A. The cross rods 180 are connected by way of clamps 181 and vertical struts 182 to the foot plate 10. In the embodiment shown in FIG. 3 and 3A, the foot plate 10 is attached to the foot support 60 solely by means of the cross rods 180 and supporting struts 182 that connect to the foot plate.

FIG. 4 is a cross sectional view from the rear of the apparatus in FIG. 3. The cross rod 180 is shown extending through the core 62 of the foot support 60. The operation of the wedge 63 is clearly shown. Also seen is an exemplary transfixation wire 16 connected by clamps 15 to foot plate 10.

Figure 5:
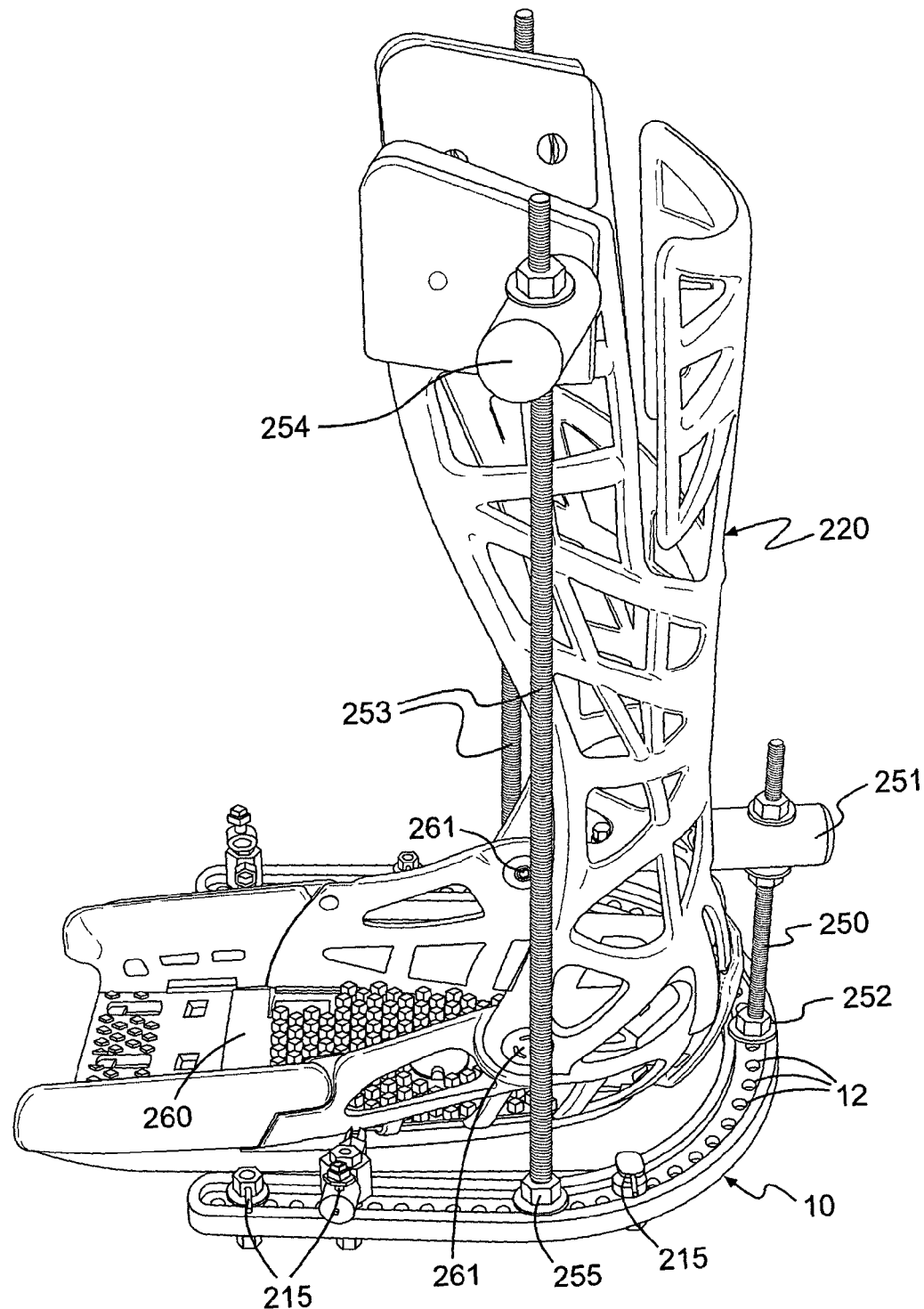
FIGS. 5 and 6 are perspective and side elevation views respectively of a third alternative embodiment of an apparatus in accordance with the present invention.
Figure 6:
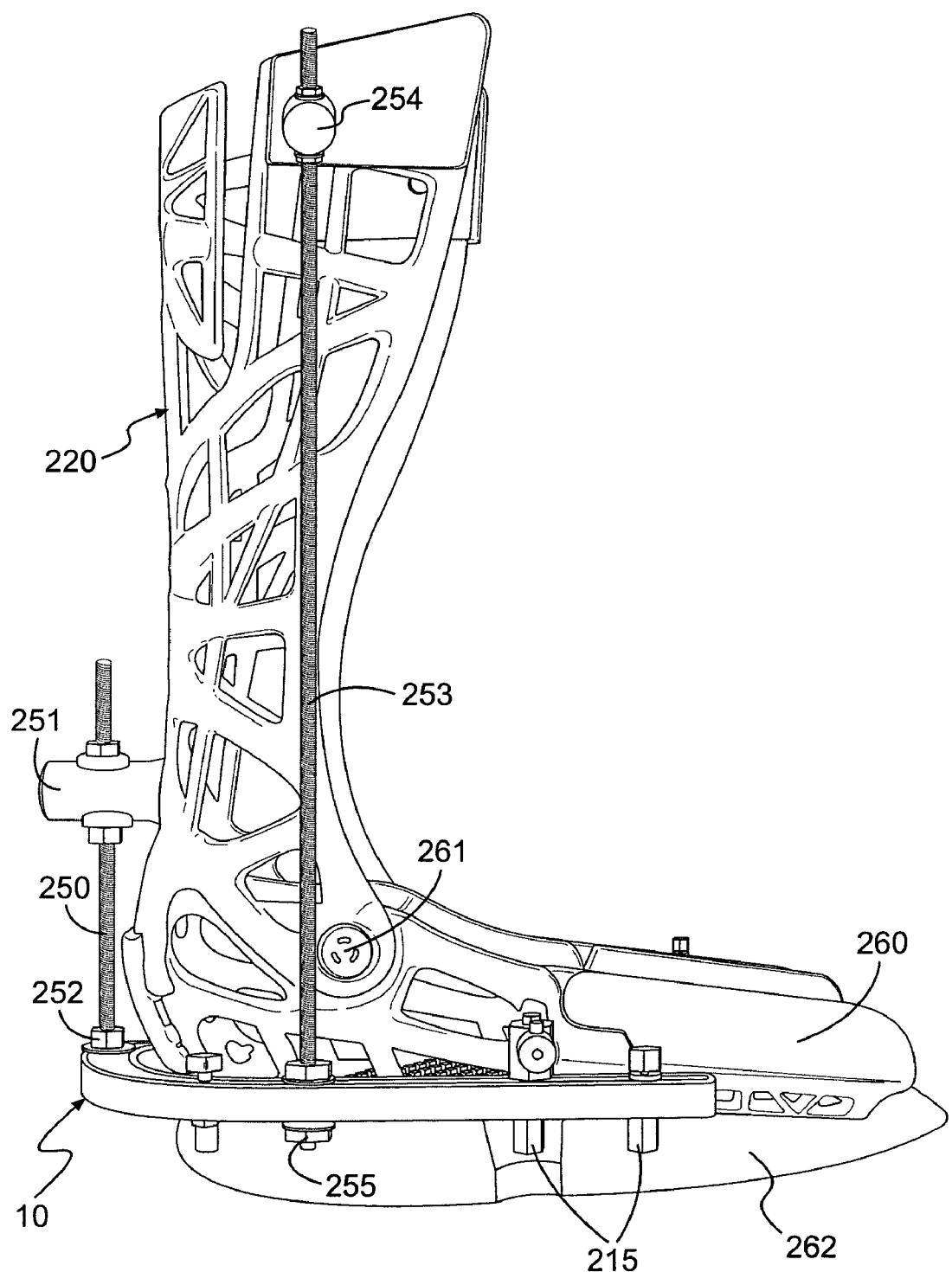

FIGS. 5 and 6 display a third alternative embodiment of an apparatus in accordance with the present invention. The leg support 220 is shown having a perforated construction that is intended to better allow air circulation around the leg of a patient wearing the brace. The leg support 220 is hingedly connected to a foot support 260 by way of hinges 261. The foot support 260 is a half-shoe type of construction adapted to support the sole of the foot of a patient. The foot support 260 may be removed and reattached from the leg support 220, or it may be permanently, hingedly connected The leg support 220 is fixed to foot plate 10 by means of side struts 253 and heel strut 250. The side struts 253 and heel strut 250 are shown as threaded metal rods. The struts 253 are connected on end to side clamps 254 which anchor the struts to the leg support 220. On the opposite end of the struts 253, there are clamps 255 that secure the struts to the foot plate 10. Variability with respect to the securing of the struts 253 to the foot plate 10 allow a doctor or surgeon to vary the angle of connection between the leg support 220 and foot plate 10. The heel strut 250 is connected on one end by clamp 251 to the posterior side of the leg support 220. The opposite end of the strut 250 is connected by a clamp 252 to the foot plate 10. By varying the height of connection of the clamp 251 on the strut 250, the angle of connection between the leg support 220 and the foot plate 10 may also be varied.

FIGS. 5 and 6 illustrate various types of clamps 215 adapted to secure transfixation wires or pins across the foot of a patient. Many different types of constructions of these clamps 215 may be used in connection with the foot plate 10. Further, variable constructions of a foot plate 10 may have variations in the types of clamps that may be used.

In the embodiment of the present invention shown in FIGS. 5 and 6, the foot support 260 includes a tread 262. The foot support 260, however, is not itself connected directly to the foot plate 10. Nevertheless, different, yet similar, types of constructions could be fashioned to connect a foot support 260 to the foot plate 10.

Also, the leg support 220 does not include any straps or foreplate as shown. These components may be added in order to secure the brace to the leg and foot of a patient.

Figure 7:
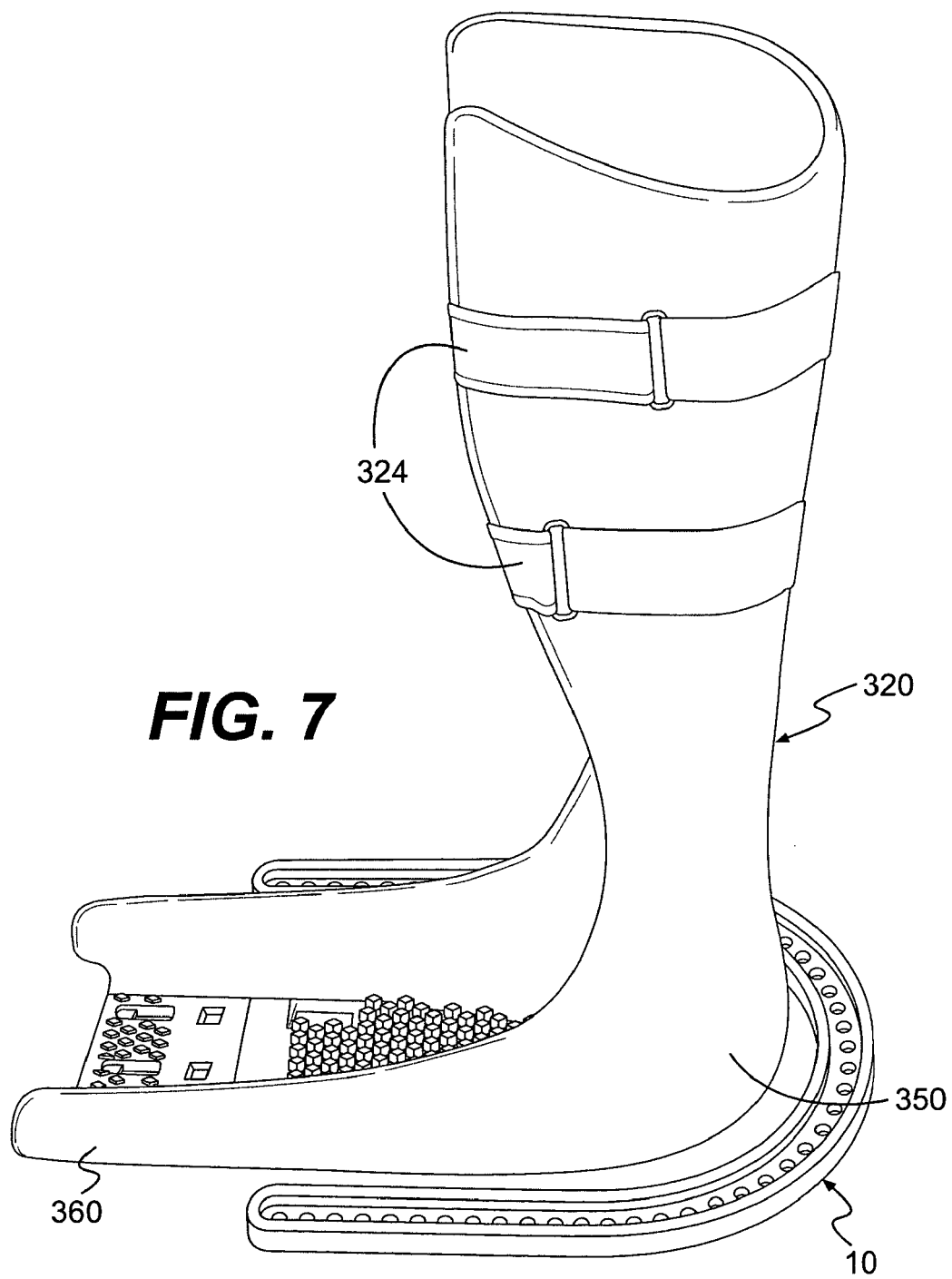
FIG. 7 is a perspective view of a fourth alternative embodiment of an apparatus in accordance with the present invention.
Figure 8:
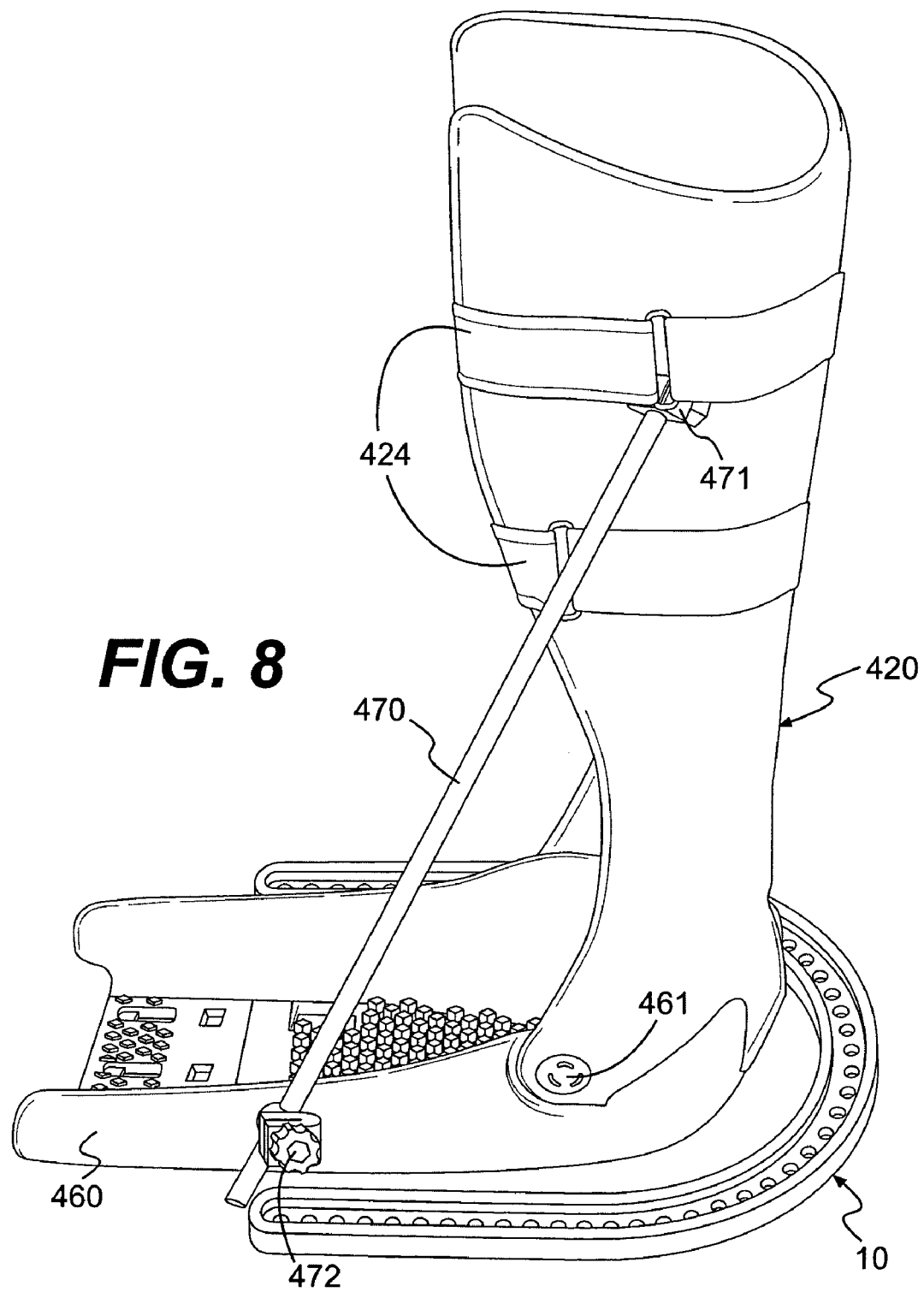
FIG. 8 is a perspective view of a fifth alternative embodiment of an apparatus in accordance with the present invention.

FIGS. 7 and 8 illustrate still further embodiments of the present invention. In these further embodiments of the present invention, the leg support is not connected to the foot plate.

In FIG. 7, leg support 320 is a unitary single piece joined together with foot support 360. The heel portion 350 of the leg support 320 is solid so that the combination of leg support 320 with foot support 360 rigidly sets the angle between the leg and foot of a patient. Accordingly, the material that makes up the leg support 320 and foot support 360, and especially the heel portion 350, must be rigid enough to handle the stresses of interaction between the leg and foot of a patient. Foot plate 10 is adapted to be positioned at least partially around the foot of a patient and further around the leg and foot support. Transfixation wires and pins may be anchored to the foot plate 10 in order to provide the purposes of the surgery.

FIG. 8 illustrates a similar type brace where the foot plate 10 is not attached in any way to the leg support 420 or foot support 460. The leg support 420 is hingedly connected to the foot support 460 around hinge 461. In order to rigidly set the angle between the foot support 460 and the leg support 420, a strut 470 is fixed on one end to the foot support and on its opposite end to the leg support. A clamp 471 attaches the strut 470 to the leg support 420. Clamp 472 connects the strut 470 to the foot support 460. Only one strut 470 is shown, but two or more may be used as needed.

The foot supports 360 and 460 in FIGS. 7 and 8 respectively do not show a thick tread/core feature, as the supports are shown to be relatively thin. Of course, an alternative construction of the foot supports 360 and 460 could include a thicker tread/core component similar to a classic cam walker boot construction. (See, for example, the tread 262 in FIG. 6.) This alternative component could be a permanent part of the supports 360 and 460 or detachable therefrom.

While the invention has been described with reference to specific embodiments thereof, it will be understood that numerous variations, modifications and additional embodiments are possible, and accordingly, all such variations, modifications, and embodiments are to be regarded as being within the spirit and scope of the invention.

What is claimed is:

1. A combination bone fixation/immobilization apparatus adapted to stabilize a patient's foot and ankle, the apparatus comprising:
   a foot plate adapted to have one or more of transfixation wires fixed thereto; and
   a substantially rigid leg support assembly adapted to receive a patient's leg, the leg support comprising a cuff and a strap adapted to secure the cuff around the patient's leg;
   wherein the leg support is rigidly attached to the foot plate;
   whereby a patient's foot may be fixed with transfixation wires, and the foot is simultaneously immobilized with respect to the ankle and lower leg.

2. An apparatus as described in claim 1 further comprising a foot support assembly rigidly attached to the foot plate and adapted to support the sole of a patient's foot.

3. An apparatus as described in claim 1, wherein the leg support includes a liner foreplate.

4. An apparatus as described in claim 2, wherein there is a variable, adjustable height connection between the foot plate and the foot support.

5. An apparatus as described in claim 1, further comprising a three-point attachment of the leg support to the foot plate.

6. An apparatus as described in claim 1, wherein the leg support further comprises a bladder filled with air, other gas, gel, foam or liquid.

7. An apparatus as described in claim 1, wherein the leg support further comprises a foam molded cushion.

8. An apparatus as described in claim 1, wherein the leg support is attached to the foot plate in a generally perpendicular position to a plane including the foot plate.

9. A combination bone fixation/immobilization apparatus adapted to stabilize a patient's foot and ankle, the apparatus comprising:
   a foot plate adapted to have one or more transfixation wires fixed thereto; and
   a substantially rigid leg support assembly adapted to receive a patient's leg, the leg support comprising a cuff and a strap adapted to secure the cuff around the patient's leg; and
   a foot support assembly rigidly attached to the leg support and adapted to support the sole of a patient's foot;
   wherein the foot plate is adapted to be positioned at least partially around and outside the leg and foot support assemblies.

10. An apparatus as described in claim 9, wherein the leg support includes a liner foreplate.

11. An apparatus as described in claim 9, wherein the leg support further comprises an bladder filled with air, other gas, gel, foam or liquid.

12. An apparatus as described in claim 9, wherein the leg support further comprises a foam molded cushion.

13. An apparatus as described in claim 9, wherein the leg support is attached to the foot plate in a generally perpendicular position to a plane including the foot plate.

14. An apparatus as described in claim 9, wherein the leg support and the foot support are a single, continuous piece.

15. An apparatus as described in claim 9, further comprising a strut connected on one end to the leg support and on the opposite end to the foot support.

16. An apparatus as described in claim 15, wherein the rigid attachment between the leg support and foot support is a hinge.

* * * * *